United States Patent
Andrews, Jr.

(10) Patent No.: US 7,111,521 B1
(45) Date of Patent: Sep. 26, 2006

(54) SAMPLING SYSTEM FOR MOVING FLUID

(75) Inventor: George A. Andrews, Jr., Fredericksburg, VA (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 11/134,603

(22) Filed: May 19, 2005

(51) Int. Cl.
*G01N 1/00* (2006.01)

(52) U.S. Cl. .................................. 73/863.41

(58) Field of Classification Search ............. 73/864.41, 73/863, 43, 863.44, 863.45, 863.51, 863.57, 73/864.51, 864.63, 863.41
See application file for complete search history.

(56) References Cited

U.S. PATENT DOCUMENTS

| | | | | |
|---|---|---|---|---|
| 3,537,316 A | * | 11/1970 | Stewart et al. | 73/170.33 |
| 3,587,323 A | * | 6/1971 | Benjaminson | 73/863.21 |
| 3,802,167 A | * | 4/1974 | Turman | 73/864.31 |
| 3,977,479 A | * | 8/1976 | Sainsbury | 175/58 |
| 4,091,835 A | * | 5/1978 | Frampton | 73/863.51 |
| 4,504,192 A | | 3/1985 | Cyrus et al. | 416/41 |
| 5,709,419 A | | 1/1998 | Roskey | 290/55 |
| 5,924,823 A | | 7/1999 | Palffy | 406/152 |
| 5,993,309 A | | 11/1999 | Howell et al. | 454/16 |
| 6,253,126 B1 | * | 6/2001 | Palmer | 701/14 |
| 6,427,543 B1 | | 8/2002 | Torrison | 73/863.33 |

* cited by examiner

*Primary Examiner*—Robert Raevis
(74) *Attorney, Agent, or Firm*—Scott R. Boalick, Esq.; Gerhard W. Thielman, Esq.

(57) ABSTRACT

A system for sampling a moving fluid utilizes a housing in the shape of an airfoil having a leading edge adapted to be disposed in the moving fluid such that the moving fluid will initially encounter the leading edge. A fluid flow pathway extends through the airfoil. One or more sampling ports are formed in the airfoil on the airfoil's high pressure side. Each sampling port is in fluid communication with the fluid flow pathway. The system can also have one or more control ports formed on the low pressure side of the airfoil. Each control port is in fluid communication with the fluid flow pathway. The housing can be mounted to experience two rotational degrees of freedom, and can have an aerodynamic tail assembly coupled thereto.

12 Claims, 1 Drawing Sheet

US 7,111,521 B1

SAMPLING SYSTEM FOR MOVING FLUID

STATEMENT OF GOVERNMENT INTEREST

The invention described herein was made in the performance of official duties by an employee of the Department of the Navy and may be manufactured, used, licensed by or for the Government for any governmental purpose without payment of any royalties thereon.

FIELD OF THE INVENTION

The invention relates generally to the sampling of moving fluids such as moving airflows, and more particularly to a sampling system that extracts samples of a moving fluid passing thereover.

BACKGROUND

Moving fluids such as airflows frequently must be sampled for a variety of flow monitoring applications. A typical sampling system utilizes a housing having (i) one or more inlets or ports formed therein, and (ii) a fan in the housing for drawing fluid moving over the housing into the ports. For relatively steady-state external flows, this type of sampling system is adequate as the system can be designed for appropriate fan power consumption and fan speeds to actualize the expected fluid flow speeds. However, if the fluid flow speed increases beyond the design parameters, the Bernoulli effect at the housing's ports causes backpressure to develop in the housing. The higher backpressure in the housing prevents the moving fluid from efficiently entering the sampling ports unless the fan speed can be increased sufficiently to overcome the backpressure. As fluid flow speeds increase, the fan can eventually overheat and fail.

SUMMARY

Accordingly, it is an object of the present invention to provide an inlet system for sampling a moving fluid.

Another object of the present invention is to provide a system that can efficiently sample a moving fluid at a variety of fluid flow speeds.

Other objects and advantages of the present invention will become more obvious hereinafter in the specification and drawings.

A system for sampling a moving fluid utilizes a housing in the shape of an airfoil having a leading edge adapted to be disposed in the moving fluid such that the moving fluid will initially encounter the leading edge of the airfoil. As a result, a high pressure side and a low pressure side of the airfoil are established. The housing further has a fluid flow pathway defined therein that starts near the leading edge and extends through the airfoil. At a minimum, one or more sampling ports are formed in the airfoil on the high pressure side. Each sampling port is in fluid communication with the fluid flow pathway.

The system can also have one or more control ports formed on the low pressure side of the airfoil aft of the leading edge thereof. Each control port is in fluid communication with the fluid flow pathway. Still further, the housing can be mounted such that it is permitted to experience two rotational degrees of freedom. An aerodynamic tail assembly can also be coupled to the housing such that, when it is disposed in the moving fluid, the tail assembly interacts with the moving fluid and causes the housing to rotate about it's mounting. As a result, the leading edge of the airfoil is always positioned to initially encounter the moving fluid for all moving fluid speeds and directions.

DETAILED DESCRIPTION

Figure 1:
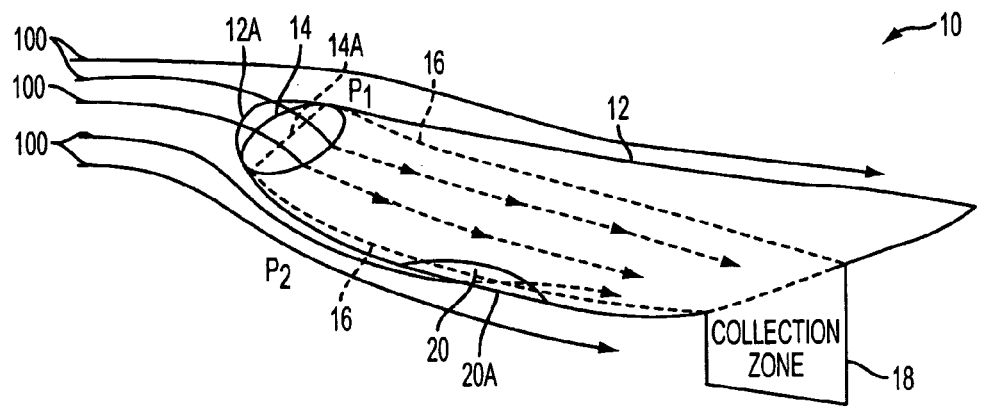
FIG. 1 is a schematic view of a moving fluid flow sampling system according to an embodiment of the present invention.

Referring now to the drawings, and more particularly to FIG. 1, a moving fluid flow sampling system in accordance with an embodiment of the present invention is shown and is referenced generally by numeral 10. In general, sampling system 10 can be used in any moving fluid environment to include liquids and gases. However, by way of example, the present invention will be described for use in a moving air environment.

Sampling system 10 utilizes an airfoil-shaped housing 12 that is placed in a moving airflow represented by flow lines 100 where the arrow heads indicate flow direction. While system 10 could utilize a variety of airfoil shapes, the shape of housing 12 should be such that, when the leading edge 12A of airfoil-shaped housing 12 is positioned such that it is the first part of housing 12 to encounter moving airflow 100, a pressure differential is established with a pressure $P_1$ on one side (e.g., the top) of housing 12 being greater than a pressure $P_2$ on the other side (e.g., the bottom). At a position aft of leading edge 12A where the pressure differential $P_1 > P_2$ is developed, at least one port 14 (e.g., one is shown) is formed in housing 12 that communicates or opens to a pathway 16 formed in and through housing 12. The exact location of port 12 is a design parameter predicated on the geometries of housing 12 and port 14. In general, pathway 16 is a non-tortuous pathway that begins with port 14 extends to a collection zone 18 located aft of leading edge 12A.

In operation, as moving airflow 100 encounters leading edge 12A and flows over housing 12 such that the pressure differential $P_1 > P_2$ develops, a portion of airflow 100 will enter port 14 (in accordance with Bernoulli's Law) and flow through pathway 16 towards collection zone 18. One or more sensors and/or measurement equipment (not shown) can be provided in collection zone 18.

Sampling system 10 can be designed for a relatively small range of airflow speeds by judicious selection of the airfoil shape of housing 12 and/or the size/number of ports 14. However, in applications where the speed of moving airflow 100 could vary beyond such design specifications, sampling system 10 can be provided with elements that allow it to adapt to speed variations. For example, one or more control ports 20 (e.g., only one is shown) can be provided on the low pressure side (i.e., on the $P_2$ side) of airfoil-shaped housing 12 aft of leading edge 12A and, typically, aft of sampling port 14. Port 20 is open to pathway 16 such that airflow in pathway 16 is always kept moving towards collection zone 18 regardless of the speed of airflow 100 at leading edge 12A.

For even greater control and adaptability, one or both of ports 14 and 20 could be adjustable in size (e.g., movable doors represented by dashed lines 14A and 20A, respectively, could be provided) so that more or less air is admitted to pathway 16. The size adjustment of port 14 and/or port 20 can be controlled passively (e.g., spring-loaded doors 14A and 20A designed to open/close by an amount based on speeds of airflow 100) or actively (e.g., a feedback system utilizing one or more sensors mounted along pathway 16 where the outputs of the sensors are supplied to controllers that control the amount of opening/closing of doors 14A and 20A).

Figure 2:
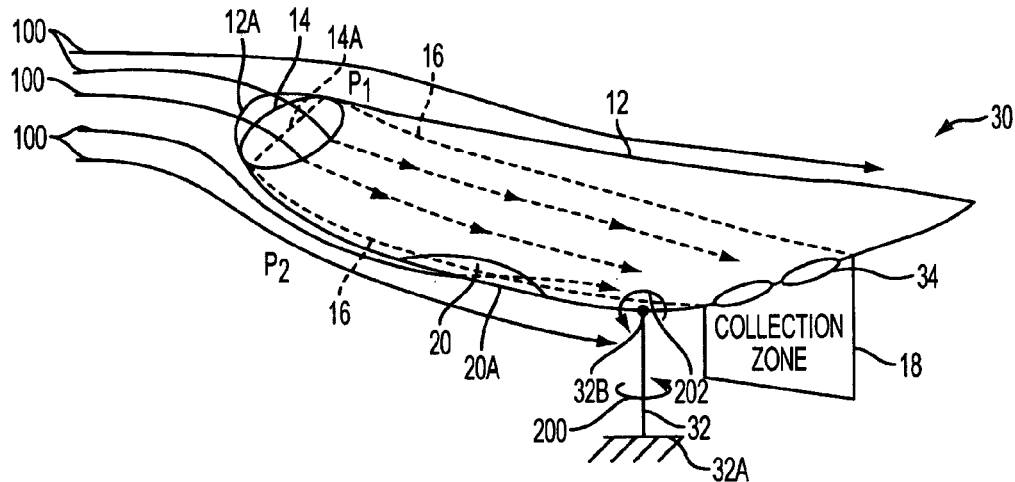
FIG. 2 is a schematic view of another embodiment of a moving fluid flow sampling system mounted for two rotational degrees of freedom.
Figure 3:
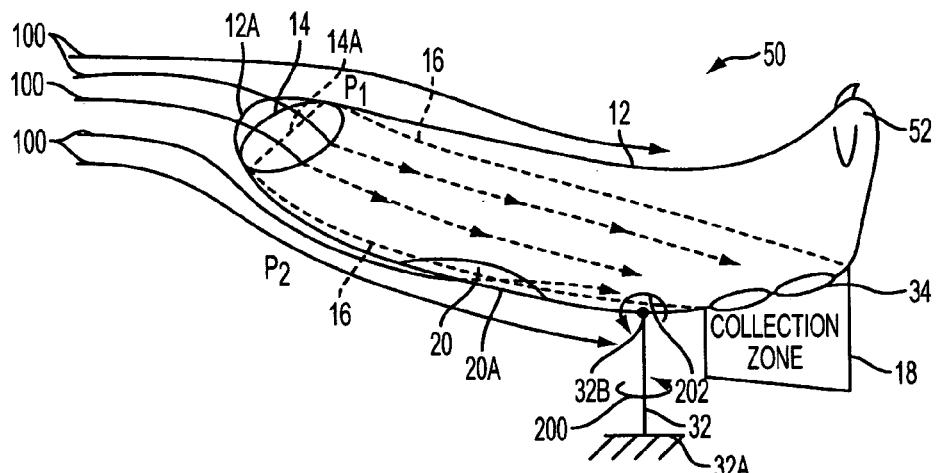
FIG. 3 is a schematic view of another embodiment of a moving fluid flow sampling system having an aerodynamic tail assembly coupled thereto.

Another embodiment of the present invention is illustrated in FIG. 2 where sampling system 30 includes the afore-described elements of system 10 and further includes a mounting 32 coupled to airfoil-shaped housing 12. More specifically, mounting 32 is fixed at 32A to some rigid structure (not shown) and is rotatably coupled to housing 12 at 32B such that housing 12 is free to experience two rotational degrees of freedom. That is, mounting 32 allows housing to rotate in azimuth thereabout as indicated by arrow 200 while simultaneously being able to pivot up or down through polar angles as indicated by arrow 202. In this way, housing 12 can adapt to changing directions of moving airflow 100 such that (i) leading edge 12A can always be positioned as the initial point-of-impact, and (ii) $P_1>P_2$.

In general, the size adjustment of port 14 and/or port 20 is used to keep sampled portions of airflow 100 moving towards collection zone 18. To further assure the movement of sampled air through pathway 16 towards collection zone 18, a fan 34 could be provided at collection zone 18. Note that since ports 14 and 20 are used to prevent any backpressure from developing in pathway 16, fan 34 could typically be a relatively low power device.

The present invention can further be adapted such that it will passively and automatically position itself optimally in a moving airflow that is also changeable in terms of its direction. For example, sampling system 50 illustrated in FIG. 3 includes the afore-described elements of system 30 and further includes an aerodynamic tail assembly 52 added to housing 12. The design of aerodynamic tail assembly 52 should be such that the forces of moving airflow 100 acting thereon control the two rotational degrees of freedom provided by mounting 32 in order to optimally position leading edge 12A relative to moving airflow 100 for the establishment of the pressure differential $P_1>P_2$. The particular design of tail assembly 52 would be well known in the art of aerodynamics and is not a limitation of the present invention.

The advantages of the present invention are numerous. For example, the backpressure problem associated with existing sampling systems is virtually eliminated. The present sampling system is readily configured to operate in fluid flows experiencing changing flow speeds and flow directions. Such operation can be passive in nature thereby making the present invention robust as well as cost effective.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed is:

1. A system for sampling a moving fluid, comprising:

a housing in the shape of an airfoil having a leading edge adapted to be disposed in a moving fluid such that the moving fluid will initially encounter the leading edge of the airfoil wherein a high pressure side and a low pressure side of the airfoil are established such that a pressure differential develops therebetween, the housing further having a fluid flow pathway defined therein that extends through the airfoil; and at least one sampling port formed in the airfoil on the high pressure side, each sampling port in fluid communication with the fluid flow pathway, wherein each sampling port comprises an adjustable-sized opening in the housing.

2. A system as in claim 1 further comprising at least one control port formed in the airfoil on the low pressure side and aft of the leading edge thereof, each control port in fluid communication with the fluid flow pathway.

3. A system as in claim 1 further comprising mounting means coupled to the housing for permitting the housing to experience two rotational degrees of freedom thereabout.

4. A system as in claim 3 further comprising an aerodynamic tail assembly coupled to the housing and adapted to be disposed in the moving fluid, the aerodynamic tail assembly interacting with the moving fluid to thereby cause the housing to rotate about the mounting means wherein the leading edge of the airfoil is positioned to initially encounter the moving fluid.

5. A system as in claim 2 wherein each control port comprises an adjustable-sized opening in the housing.

6. A system for sampling a moving fluid, comprising:

a housing in the shape of an airfoil having a leading edge adapted to be disposed in a moving fluid such that the moving fluid will initially encounter the leading edge of the airfoil wherein a high pressure side and a low pressure side of the airfoil are established such that a pressure differential develops therebetween, the housing further having a fluid flow pathway defined therein that extends trough the airfoil to a collection zone;

at least one sampling port formed in the airfoil on the high pressure side, each sampling port in fluid communication with the fluid flow pathway;

at least one control port formed in the airfoil on the low pressure side and aft of the sampling port, each control port in fluid communication with the fluid flow pathway; and mounting means coupled to the housing for permitting the housing to experience two rotational degrees of freedom thereabout, wherein a portion of the moving fluid is drawn into each sampling port and travels through the fluid flow pathway to the collection zone.

7. A system as in claim 6 further comprising an aerodynamic tail assembly coupled to the housing and adapted to be disposed in the moving fluid, the aerodynamic tail assembly interacting with the moving fluid to thereby cause the housing to rotate about the mounting means wherein the leading edge of the airfoil is positioned to initially encounter the moving fluid.

8. A system as in claim 6 wherein each sampling port comprises an adjustable-sized opening in the housing.

9. A system as in claim 6 wherein each control port comprises an adjustable-sized opening in the housing.

10. A system as in claim 6 further comprising a fan mounted in the housing at the collection zone.

11. A system for sampling a moving fluid, comprising:

a housing in the shape of an airfoil having a leading edge adapted to be disposed in a moving fluid such that the moving fluid will initially encounter the leading edge of the airfoil wherein a high pressure side and a low pressure side of the airfoil are established such that a pressure differential develops therebetween, the housing further having a fluid flow pathway defined therein that extends through the airfoil to a collection zone;
at least one adjustable-sized sampling port formed in the airfoil on the high pressure side, each sampling port in fluid communication with the fluid flow pathway;
at least one adjustable-sized control port formed in the airfoil on the low pressure side and aft of the sampling port, each control port in fluid communication with the fluid flow pathway;
mounting means coupled to the housing for permitting the housing to experience two rotational degrees of freedom thereabout, wherein a portion of the moving fluid is drawn into each sampling port and travels through the fluid flow pathway to the collection zone; and
an aerodynamic tail assembly coupled to the housing and adapted to be disposed in the moving fluid, the aerodynamic tail assembly interacting with the moving fluid to thereby cause the housing to rotate about the mounting means wherein the leading edge of the airfoil is positioned to initially encounter the moving fluid.

12. A system as in claim 11 further comprising a fan mounted in the housing at the collection zone.

* * * * *